(12) United States Patent
Yin

(10) Patent No.: US 10,487,133 B2
(45) Date of Patent: Nov. 26, 2019

(54) CODON OPTIMIZATION FOR TITER AND FIDELITY IMPROVEMENT

(71) Applicant: Sutro Biopharma, Inc., South San Francisco, CA (US)

(72) Inventor: Gang Yin, South San Francisco, CA (US)

(73) Assignee: Sutro Biopharma, Inc., South San Francisco, CA (US)

( * ) Notice: Subject to any disclaimer, the term of this patent is extended or adjusted under 35 U.S.C. 154(b) by 0 days.

(21) Appl. No.: 15/537,290

(22) PCT Filed: Dec. 18, 2015

(86) PCT No.: PCT/US2015/066823
§ 371 (c)(1),
(2) Date: Jun. 16, 2017

(87) PCT Pub. No.: WO2016/100889
PCT Pub. Date: Jun. 23, 2016

(65) Prior Publication Data
US 2018/0051065 A1 Feb. 22, 2018

Related U.S. Application Data

(60) Provisional application No. 62/094,767, filed on Dec. 19, 2014.

(51) Int. Cl.
| | | |
|---|---|---|
| *C07K 1/02* | (2006.01) | |
| *C12N 15/67* | (2006.01) | |
| *C07K 14/71* | (2006.01) | |
| *C12P 21/02* | (2006.01) | |
| *C07K 1/00* | (2006.01) | |

(52) U.S. Cl.
CPC .............. *C07K 14/71* (2013.01); *C07K 1/003* (2013.01); *C07K 1/006* (2013.01); *C07K 1/02* (2013.01); *C12N 15/67* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 2013/0164270 A1 | 6/2013 | Keshet et al. | |
| 2013/0281667 A1* | 10/2013 | Wei | C07K 14/56 530/351 |
| 2014/0288163 A1* | 9/2014 | Levy | A61K 31/522 514/44 R |

FOREIGN PATENT DOCUMENTS

WO 2014/172631 A2 10/2014

OTHER PUBLICATIONS

International Search Report and Written Opinion for International Application No. PCT/US15/66823 dated Mar. 7, 2016, 10 pages.
Bennetzen et al., "Codon Selection in Yeast", The Journal of Biological Chemistry, vol. 257, No. 6, Mar. 25, 1982, pp. 3026-3031.
Campbell et al., "Codon Usage in Higher Plants, Green Algae, and Cyanobacteria", Plant Physiology, American Society of Plant Biologists, vol. 92, No. 1, Jan. 1, 1990, pp. 1-11.
Denis et al., "A Positive Regulatory Gene is Required for Accumulation of the Functional Messenger RNA for the Glucose-repressible Alcohol Dehydrogenase from *Saccharomyces cerevisiae*", Journal of Molecular Biology, Academic Press, vol. 148, No. 4, Jun. 5, 1981, pp. 355-368.
Oh et al., "Cell-Free Production of Functional Antibody Fragments", Bioprocess and Biosystems Engineering, vol. 33, No. 1, Jan. 1, 2010, pp. 127-132.
Oh et al., "Providing an Oxidizing Environment for the Cell-Free Expression of Disulfide-Containing Proteins by Exhausting the Reducing Activity of *Escherichia coli* S30 Extract", Biotechnology Progress, American Institute of Chemical Engineers, vol. 22, No. 4, 2006, pp. 1225-1228.
Yu, "Identification of Codon-Specific Serine to Asparagine Mistranslation in Recombinant Monoclonal Antibodies by High-Resolution Mass Spectrometry", Analytical Chemistry, American Chemical Society, vol. 81, No. 22, Nov. 15, 2009, pp. 9282-9290.
EP15871212.5, "Extended European Search Report", dated Jun. 25, 2018, 9 pages.

* cited by examiner

*Primary Examiner* — Nancy A Treptow
(74) *Attorney, Agent, or Firm* — Kilpatrick Townsend & Stockton LLP

(57) ABSTRACT

The invention provides methods for producing a protein in a cell free protein synthesis system such that the protein does not contain an asparagine (Asn or N) residue at serine (Ser or S) positions. Also provided are compositions and nucleic acid templates for use in the methods described herein.

26 Claims, 9 Drawing Sheets

| SP-007144 | Original sequence v1 | | | | Codon optimized v2 (-AGC) | | | |
|---|---|---|---|---|---|---|---|---|
| | HC | | LC | | HC | | LC | |
| | # | % | # | % | # | % | # | % |
| AGT | 0 | 0% | 0 | 0% | 0 | 0% | 0 | 0% |
| AGC | 34 | 65% | 20 | 61% | 0 | 0% | 0 | 0% |
| TCG | 3 | 6% | 2 | 7% | 13 | 25% | 8 | 27% |
| TCA | 1 | 2% | 1 | 3% | 13 | 25% | 7 | 23% |
| TCT | 6 | 12% | 3 | 10% | 14 | 27% | 7 | 23% |
| TCC | 8 | 15% | 4 | 13% | 12 | 23% | 8 | 27% |

FIG. 1

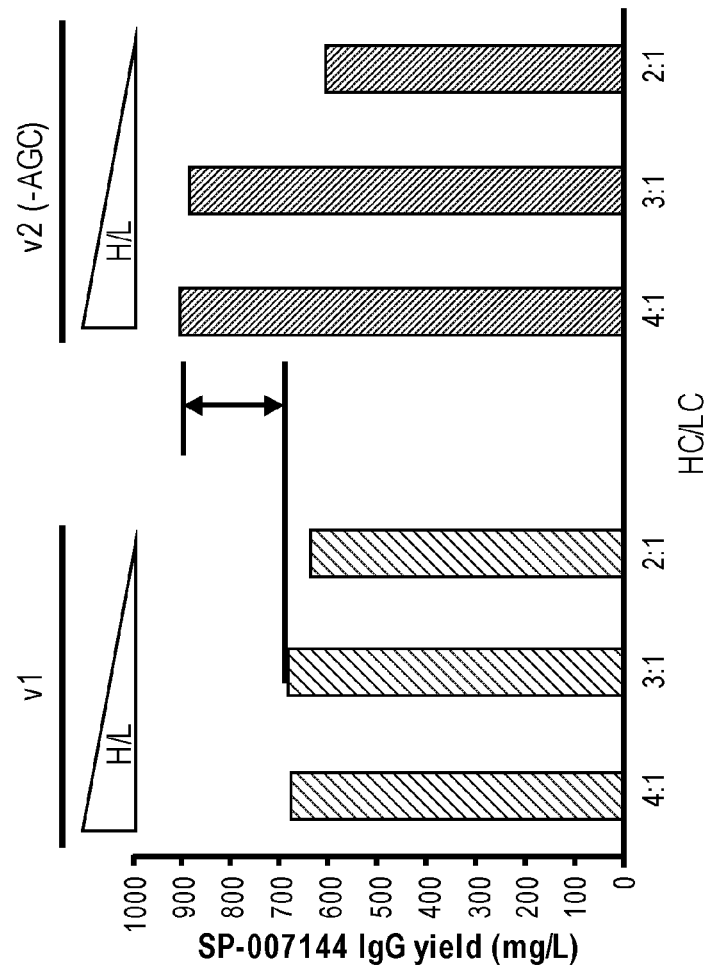
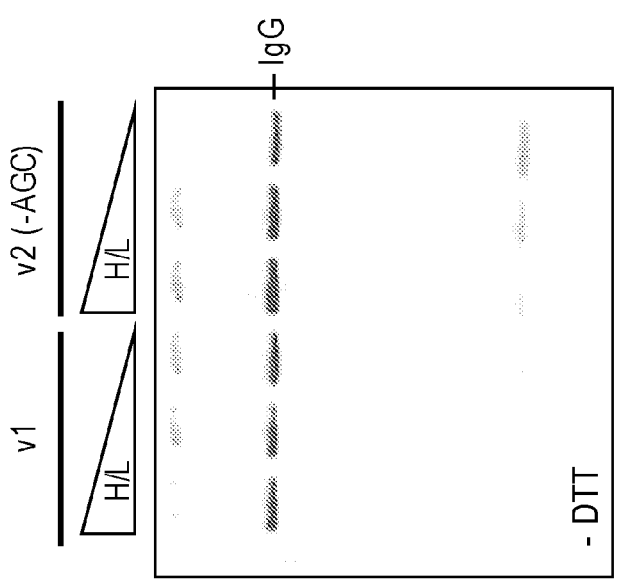
FIG. 2C
FIG. 2A
FIG. 2B

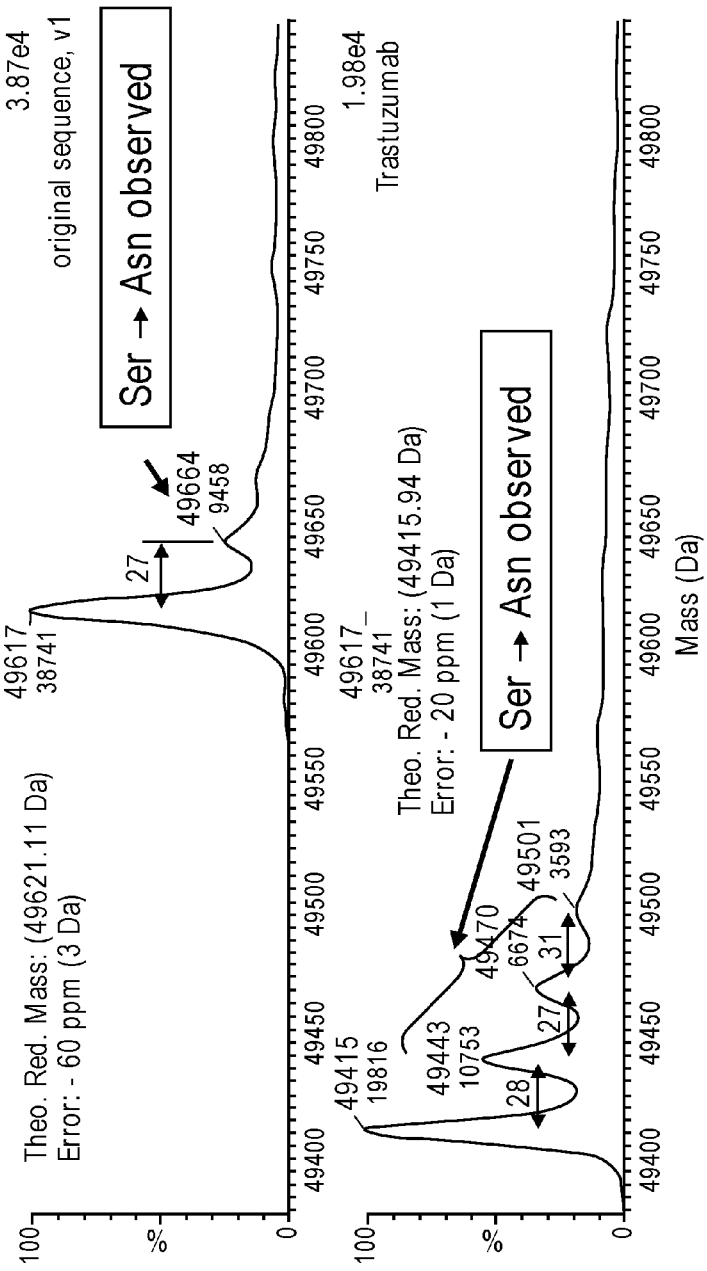

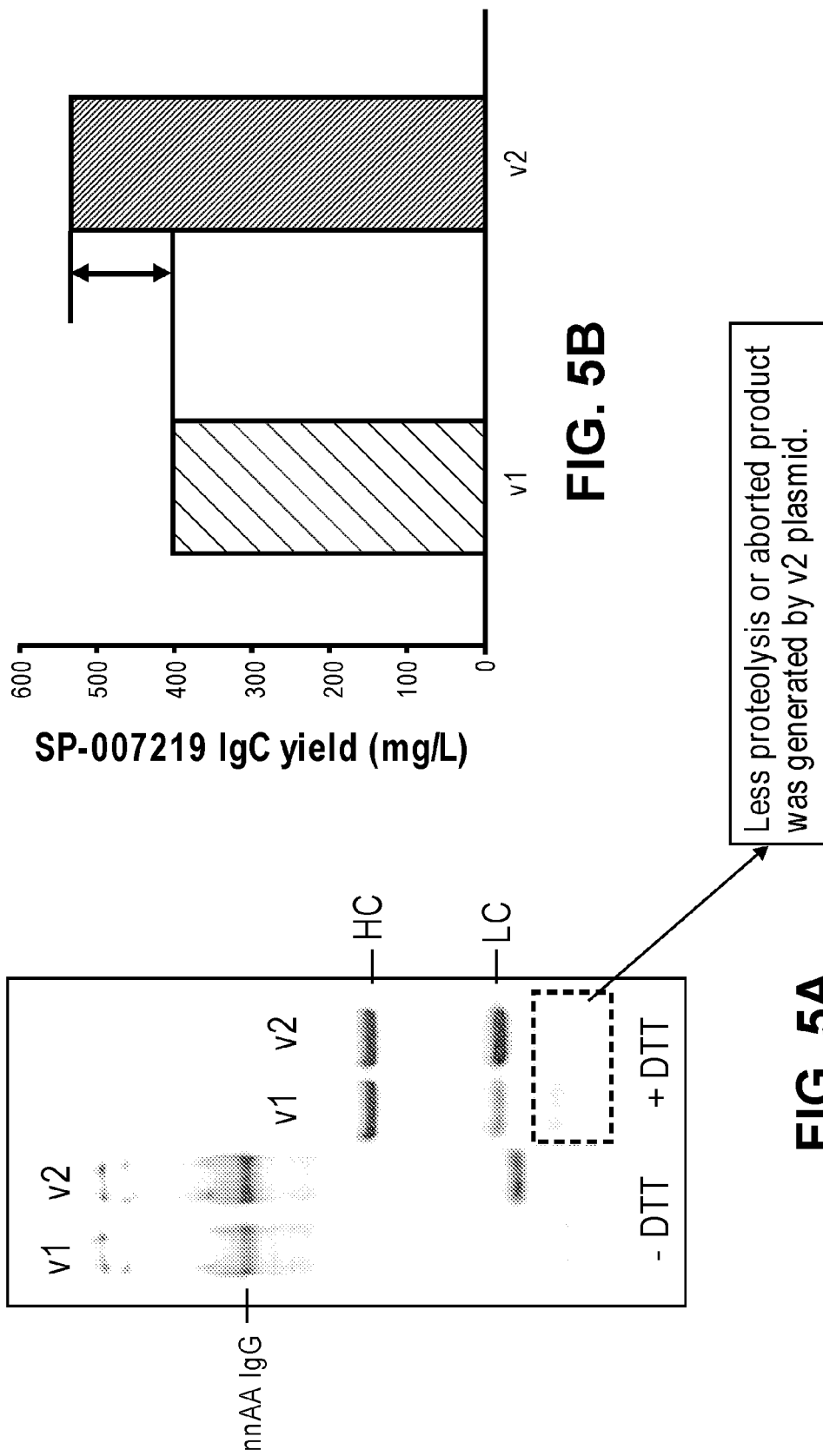

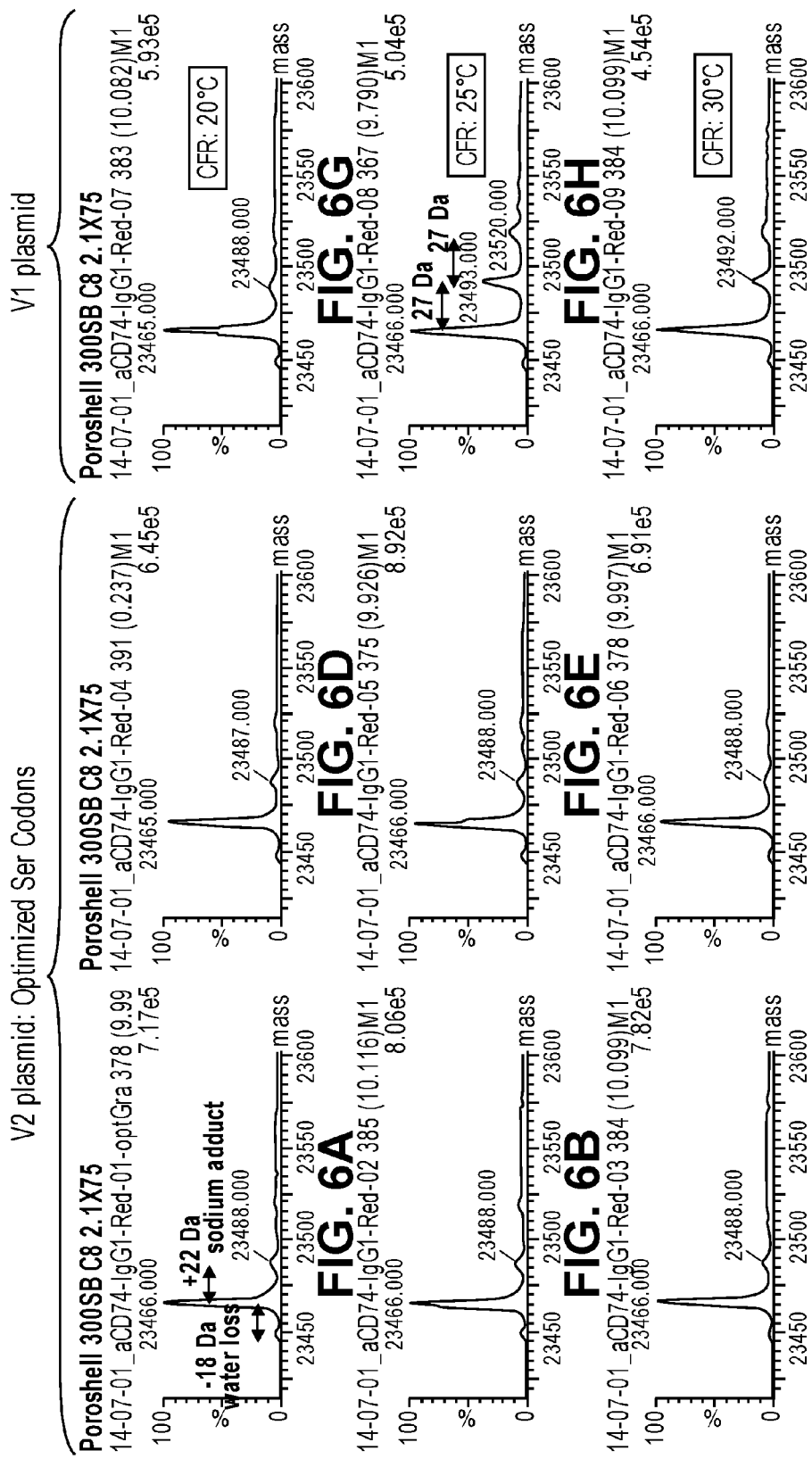

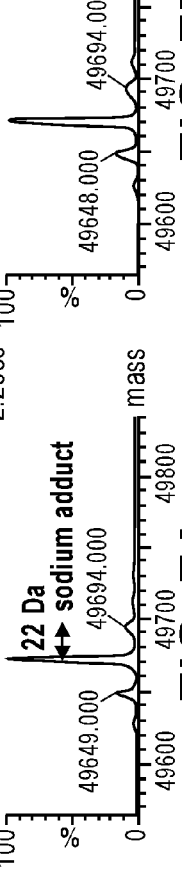
FIG. 7A — FIG. 7I

CODON OPTIMIZATION FOR TITER AND FIDELITY IMPROVEMENT

CROSS-REFERENCES TO RELATED APPLICATIONS

This application is the U.S. National Stage Entry under § 371 of International Application No. PCT/US2015/066823, filed Dec. 18, 2015, which claims the benefit of U.S. Provisional Application No. 62/094,767, filed Dec. 19, 2014, the disclosure of which is herein incorporated by reference in its entirety for all purposes.

FIELD OF THE INVENTION

This invention relates to compositions and methods for producing a protein of interest having multiple serine residues in a cell free protein synthesis (CFPS) system. By avoiding the use of the most common codon encoding serine, the present invention advantageously provides increased protein production and improved fidelity. The present invention also provides greater ease in maximizing protein production.

BACKGROUND OF THE INVENTION

The use of recombinant proteins as therapeutics to combat disease is of great interest. For therapeutic use, the proteins must be produced and manufactured safely, efficiently and consistently. Furthermore, methods resulting in high protein yields and high translational fidelity are crucial to developing therapeutic proteins.

Unfortunately, errors in protein synthesis such as misincorporation of amino acids into the nascent polypeptide chain thereby generating sequence variations in the target protein can arise at any stage of gene expression. It has been estimated that error rates in typical cells are about 1 in $10^8$ for DNA replication by *E. coli*, about 1 in $10^5$ bases for transcription in *E. coli* and about 1 in $10^4$ for codon translation in proteins produced in *E. coli* or other mammalian expression systems (Reynolds et al., *Nat Rev Microbiol*, 2010, 8:849-856; Kunkel, T A, *J Biol Chem*, 2004, 279: 16895-16898; Rosenberge et al., *Mol Gen Genet*, 1981, 183:561-563; Blank et al., *Biochemistry*, 1986, 25:5920-5928; Kramer et al., *RNA*, 2007, 13: 87-96). In addition, error rates can be increased under stress conditions, such as during amino acid starvation (Parker et al., *Proc Natl Acad Sci USA*, 1978, 75:1091-1095) and in protein expression systems (Scorer et al., *Nucleic Acids Res*, 1991, 19:3511-3516). For example, in heterologous expression systems for overexpressing recombinant proteins, host cells undergo nutritional stress which in turn leads to increased amino acid misincorporation during translation. The undesired amino acid substitution can result in proteins with altered catalytic constants, specificity, and stability (Langridge, J, *Aust J Biol Sci*, 1974, 27:309-319; Nene et al., *Mol Gen Genet*, 1984, 194:166-172; Knowles J R, *Science*, 1987, 236:1252-1258; and Cupples et al., *Genetics*, 1988, 120:637-644). Amino acid error in therapeutic proteins can potentially induce deleterious immune responses and abnormal protein-protein interactions. Methods for removing misincorporated proteins have proven to be difficult during downstream purification schemes, especially since the error-free proteins are typically several orders of magnitude higher in concentration than the proteins containing misincorporations (Huang et al., *Protein Sci*, 2012, 21(5):625-632).

Misincorporation of serine residues for other amino acid residues, e.g., asparagine residues has been detected in antibodies (Shulman et al., *Proc Natl Acad Sci USA*, 1986, 83:7678-7682). Recombinant antibodies containing erroneous asparagine residues may exhibit altered structural and functional features, including altered sensitivity to proteolysis, reduced biological activity or increased immunogenicity (Yu et al., *Analytical Chemistry*, 81(22):9282-9290. Thus, there is a need for methods and compositions for producing proteins (e.g., antibodies) that are free of amino acid misincorporations. Such methods should generate high protein yields and maintain high translational fidelity. The present invention satisfies this need as well as others.

BRIEF SUMMARY OF THE INVENTION

In one aspect, the present invention provides a method for producing a protein of interest in a cell free protein synthesis system wherein said protein has multiple serine residues. The method includes (i) combining a nucleic acid template encoding the protein with a cell free synthesis system, wherein the template comprises codons encoding serine residues and wherein no more than 10%, e.g., 9%, 8%, 7%, 6%, 5%, 4%, 3%, 2%, 1% or less of the codons encoding serine residues are AGC, and (ii) incubating the template and the cell free synthesis system under conditions permitting the translation (production or synthesis) of the protein of interest.

In some embodiments, the cell free protein synthesis system is derived from a bacterial cell. In some instances, the bacterial cell is an *E. coli* cell. In some embodiments, the cell free protein synthesis system has an active oxidative phosphorylation system.

In some embodiments, the protein of interest is an antibody or a fragment thereof. In some instances, the antibody is IgG or IgE.

In some embodiments, the protein of interest is produced at a concentration of greater than 6 mg/L, e.g., 7 mg/L, 10 mg/L, 50 mg/L, 100 mg/L, 150, mg/L, 200 mg/L, 250 mg/L, 300 mg/L, 350 mg/L, 400 mg/L, 450 mg/L, 500 mg/L, 550 mg/L, 600 mg/L, 650 mg/L, 700 mg/L, 750 mg/L, 800 mg/L, 850 mg/L, 900 mg/L, 950 mg/L, 1000 mg/L or more. In other embodiments, the protein of interest is produced at a concentration (amount or level) of greater than 1000 mg/L, e.g., 1100 mg/L, 1200 mg/L, 1300 mg/L, 1400 mg/L, 1500 mg/L, 1600 mg/L, 1700 mg/L, 1800 mg/L, 1900 mg/L, 2000 mg/L, or more.

In some embodiments, the protein of interest comprises amino acids wherein more than 15%, e.g., 16%, 17%, 18%, 19%, 20% or more of the amino acids are serine residues. In other embodiments, the protein of interest comprises amino acids wherein more than 20%, e.g., 21%, 22%, 23%, 24%, 25%, 26%, 27%, 28%, 29%, 30%, or more of the amino acids are serine residues.

In some embodiments, the codons encoding serine are selected from the group comprising of AGT, TCA, TCC, TCG and TCT. In other embodiments, the codons encoding serine are selected from the group comprising of TCA, TCC, TCG and TCT.

In some embodiments, the nucleic acid template has no AGC codons. In some instances, the nucleic acid template has no AGT codons.

In another aspect, the present invention provides a combination of a nucleic acid template and a cell free protein synthesis system for producing a protein of interest having a plurality of serine residues. The combination includes a nucleic acid template encoding the protein of interest, wherein the nucleic acid template comprises codons encoding serine residues and wherein no more than 10%, e.g., 9%, 8%, 7%, 6%, 5%, 4%, 3%, 2%, 1% or less of the codons encoding the serine residues are AGC; and a cell free synthesis system. In some cases, none of the codons encoding the serine residues are AGC.

In some embodiments, the cell free protein synthesis system is derived from a bacterial cell. In some instances, the bacterial cell is an *E. coli* cell. In some embodiments, the cell free protein synthesis system has an active oxidative phosphorylation system.

In some embodiments, the protein of interest is an antibody or a fragment thereof. In some instances, the antibody is IgG or IgE.

In some embodiments, the protein of interest is produced at a concentration of greater than 6 mg/L, e.g., 7 mg/L, 10 mg/L, 50 mg/L, 100 mg/L, 150, mg/L, 200 mg/L, 250 mg/L, 300 mg/L, 350 mg/L, 400 mg/L, 450 me/L, 500 mg/L, 550 mg/L, 600 mg/L, 650 mg/L, 700 mg/L, 750 mg/L, 800 mg/L, 850 mg/L, 900 mg/L, 950 mg/L, 1000 mg/L or more. In other embodiments, the protein of interest is produced at a concentration (amount or level) of greater than 1000 mg/L, e.g., 1100 mg/L, 1200 mg/L, 1300 mg/L, 1400 mg/L, 1500 mg/L, 1600 mg/L, 1700 mg/L, 1800 mg/L, 1900 mg/L, 2000 mg/L, or more.

In some embodiments, the protein of interest comprises amino acids wherein more than 15%, e.g., 16%, 17%, 18%, 19%, 20% or more, of the amino acids are serine residues. In other embodiments, the protein of interest comprises amino acids wherein more than 20%, e.g., 21%, 22%, 23%, 24%, 25%, 26%, 27%, 28%, 29%, 30%, or more of the amino acids are serine residues.

In some embodiments, the codons encoding serine are selected from the group comprising of AGT, TCA, TCC, TCG and TCT. In other embodiments, the codons encoding serine are selected from the group comprising of TCA, TCC, TCG and TCT.

In some embodiments, the nucleic acid template has no AGC codons. The nucleic acid template may also have no AGT codons.

In yet another aspect, the present invention provides a nucleic acid encoding a protein of interest having a plurality of serine residues, wherein the nucleic acid comprises codons encoding serine residues and wherein no more than 10%, e.g., 9%, 8%, 7%, 6%, 5%, 4%, 3%, 2%, 1% or less of the codons encoding the serine residues are AGC.

In some embodiments, the protein of interest is an antibody or a fragment thereof. In some instances, the antibody is IgG or IgE.

In some embodiments, the protein of interest is produced at a concentration of greater than 6 mg/L, e.g., 7 mg/L, 10 mg/L, 50 mg/L, 100 mg/L, 150, mg/L, 200 mg/L, 250 mg/L, 300 mg/L, 350 mg/L, 400 mg/L, 450 mg/L, 500 mg/L, 550 mg/L, 600 mg/L, 650 mg/L, 700 mg/L, 750 mg/L, 800 mg/L, 850 mg/L, 900 mg/L, 950 mg/L, 1000 mg/L or more. In other embodiments, the protein of interest is produced at a concentration (amount or level) of greater than 1000 mg/L, e.g., 1100 mg/L, 1200 mg/L, 1300 mg/L, 1400 mg/L, 1500 mg/L, 1600 mg/L, 1700 mg/L, 1800 mg/L, 1900 mg/L, 2000 mg/L, or more.

In some embodiments, the protein of interest comprises amino acids wherein more than 15%, e.g., 16%, 17%, 18%, 19%, 20% or more, of the amino acids are serine residues. In other embodiments, the protein of interest comprises amino acids wherein more than 20%, e.g., 21%, 22%, 23%, 24%, 25%, 26%, 27%, 28%, 29%, 30%, or more of the amino acids are serine residues.

In some embodiments, the codons encoding serine are selected from the group comprising of AGT, TCA, TCC, TCG and TCT. In other embodiments, the codons encoding serine are selected from the group comprising of TCA, TCC, TCG and TCT.

In some embodiments, the nucleic acid template has no AGC codons. The nucleic acid template may also have no AGT codons.

Provided herein are methods and compositions based, in part, on the unexpected discovery that eliminating the serine AGC codon in a nucleic acid template encoding a protein of interest increases the yield of protein in cell free protein synthesis (CFPS) reactions. In some embodiments, the protein titer increases by at least about 30/% compared to a corresponding nucleic acid template encoding the protein of interest and containing AGC codons. The method and compositions described herein are useful to generate proteins of interest using CFPS without producing a proteolytic product, synthesis aborted product or prematurely terminated protein product.

Other objects, features, and advantages of the present invention will be apparent to one of skill in the art from the following detailed description and figures.

BRIEF DESCRIPTION OF THE DRAWINGS

FIG. 1 illustrates the elimination of the S to N substitution (serine to asparagine substitution) when the serine codon AGC is avoided and the other serine codons are used evenly in the nucleic acid template for cell free protein synthesis. "v2 (-AGC) HC" represents a codon optimized template encoding a trastuzumab heavy chain and "v2 (-AGC) LC" represents a codon optimized template encoding a trastuzumab light chain.

FIGS. 2A-2C show that the protein yield was improved by about 30% when the serine codon optimized plasmid was used for CFPS. About 6-7 fold less proteolysis or aborted protein product was detected from the plasmid that contains no serine AGC codons (v2 (-AGC) HC/LC)). FIG. 2A shows a non-reducing SDS-PAGE of the synthesized samples. FIG. 2B shows a reducing SDS-PAGE of the synthesized samples treated with DTT. FIG. 2C shows a graph of the protein yield (mg/L) for different ratios of the trastuzumab heavy chain template and light chain template (e.g., HC:LC ratios of 4:1, 3:1, and 2:1).

FIGS. 3A-3C provide mass spectrometry data that shows the presence or absence of a S to N substitution (serine to asparagine substitution) in the trastuzumab heavy chain produced in a cell free protein synthesis reaction. The S to N (Ser to Asn) substitution was observed in the trastuzumab control (FIG. 3C) and the original sequence of the trastuzumab heavy chain (FIG. 3B). The amino acid substitution was not detected from the codon optimized nucleic acid template (FIG. 3A).

FIGS. 5A and 5B illustrate that protein yield was improved when a nucleic acid template containing no serine AGC codons was used to synthesis a pAMF incorporated anti-CD74 IgG in a CFPS reaction. Less proteolysis or aborted protein product was generated from the codon optimized nucleic acid template. FIG. 5A shows a SDS-PAGE of the non-native amino acid containing antibody under non-reducing conditions and the corresponding heavy chain and light chain under reducing conditions (e.g., treatment with DTT). FIG. 5B shows that more pAMF-anti-CD74 IgG protein was synthesized from the nucleic acid template that contains no serine AGC codons and that uses the other serine codons evenly in the template.

FIGS. 6A-6I show mass spectrometry data depicting the lack of S to N substitutions (serine to asparagine substitutions) from codon optimized nucleic acid templates in CFPS reactions performed at 20° C., 25° C. and 30° C., and with heavy chain plasmid to light chain plasmid ratios (H:L) of 3:1 and 6:1. The data shows that antibody light chains synthesized from the wild-type (original) plasmid that contains serine AGC codons produced a S to N substitution when the CFPS reaction temperature was 25° C. (FIG. 6H) and 30° C. (FIG. 6I). The misincorporation was not seen at the reaction temperature of 20° C. (FIG. 6G). The serine codon optimized templates did not produce light chains with the S to N substitution (FIGS. 6A-F) at any of the reaction temperatures or heavy chain plasmid:light chain plasmid ratios. Data for the codon optimized nucleic acid templates used at a H:L ratio of 3:1 and a CFPS reaction temperature of 20° C., 25° C. and 30° C. are shown in FIGS. 6A, 6B and 6C, respectively. Data for the codon optimized nucleic acid templates used at a H:L ratio of 6:1 and a CFPS reaction temperature of 20° C., 25° C. and 30° C. are shown in FIGS. 6D, 6E and 6F, respectively.

FIGS. 7A-7I show mass spectrometry data demonstrating the absence of asparagine residues at serine positions in antibody heavy chains produced from codon optimized nucleic acid templates in CFPS reactions performed at 20° C., 25° C. and 30° C. The data also shows that antibody heavy chains synthesized from the wild-type (original or non codon optimized) plasmid contain the amino acid substitution when the CFPS reaction temperature was 25° C. (FIG. 7H) or 30° C. (FIG. 7I). The substitution was not detected when the reaction was performed at 20° C. (FIG. 7G). The S to N misincorporation was not observed in any of the conditions tested when the serine codon optimized template was used (FIGS. 7A-7F). Data for the codon optimized nucleic acid templates used at a H:L ratio of 3:1 and a CFPS reaction temperature of 20° C., 25° C. and 30° C. are shown in FIGS. 7A, 7B and 7C, respectively. Data for the codon optimized nucleic acid templates used at a H:L ratio of 6:1 and a CFPS reaction temperature of 20° C., 25° C. and 30° C. are shown in FIGS. 7D, 7E and 7F, respectively.

FIG. 8 shows that the trastuzumab heavy chain and light chain generated from the serine optimized genes underwent less proteolysis and generated fewer aborted expression products, compared those generated from the wild-type (non optimized) genes.

FIG. 9 also shows that the maximal yield of trastuzumab was produced when the ratio of heavy chain serine optimized gene to light chain serine optimized gene was 1:1.

DETAILED DESCRIPTION OF THE INVENTION

I. Definitions

Figure 4C:
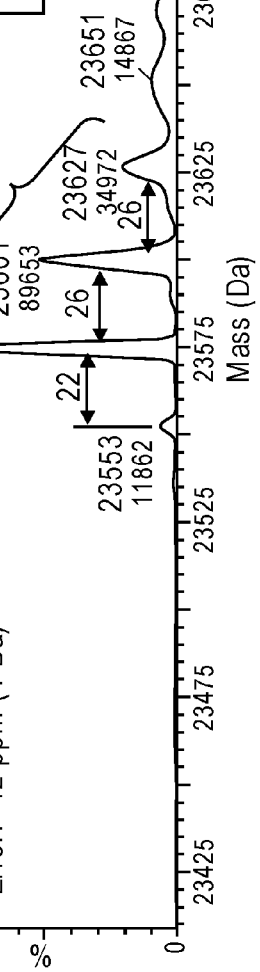
FIGS. 4A-4C provide mass spectrometry data showing the presence or absence of a serine to asparagine substitution in the trastuzumab light chain produced in a cell free synthesis reaction. The amino acid misincorporation was observed in the trastuzumab control (FIG. 4C) and the original (wild-type or non optimized) sequence of the trastuzumab light chain (FIG. 4B). The amino acid substitution was not detected from the serine codon optimized nucleic acid template (FIG. 4A).
Figure 4A:
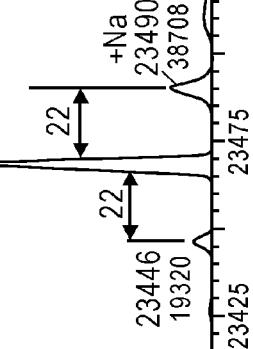
Figure 4B:
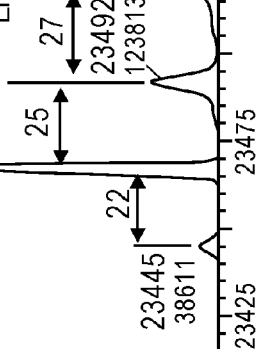

As used herein, the following terms have the meanings ascribed to them unless specified otherwise.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a," "and," and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

The term "bacterial extract" refers to a bacterial cell lysate or a fraction thereof wherein the cellular extract is able to synthesis a protein from a nucleic acid template without adding other components. In other words, the bacterial extract contains an energy source, such as ATP, GTP and the like. A bacterial extract can be a portion of a lysate from which other cellular components of the lysate have been separated by centrifugation, filtration, selective precipitation, selective immunoprecipitation, chromatography, or other methods. It also includes lysates or fractions thereof that contain exogenous material such as preservatives, stabilizers and reagents that enhance cell free protein synthesis (CFPS). The term "bacterial extract" can refer to a preparation of an in vitro reaction mixture able to transcribe DNA into mRNA and/or translate mRNA into polypeptides. The mixture may include ribosomes, ATP, amino acids, and tRNAs. The mixture may be derived directly from lysed bacteria, from purified components or combinations of both. The mixture may also include an exogenous energy source, such as pyruvate, glutamate, glucose, or the like.

The term "lysate" is any cell derived preparation comprising the components required for protein synthesis machinery, wherein such cellular components are capable of expressing a nucleic acid encoding a desired protein where a majority of the biological components are present in concentrations resulting from the lysis of the cells rather than having been reconstituted. A lysate may be further altered such that the lysate is supplemented with additional cellular components, e.g. amino acids, nucleic acids, enzymes, etc. The lysate may also be altered such that additional cellular components are removed or degraded following lysis.

"Cell free protein synthesis" or "CFPS" refers to the in vitro synthesis of nucleic acids, polypeptides, small molecules and/or viral particles in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc.; and co-factors, enzymes and other reagents that are necessary for the synthesis, e.g. ribosomes, uncharged tRNAs, tRNAs charged with natural and/or unnatural amino acids, polymerases, transcriptional factors, tRNA synthetases, etc.

The term "active oxidative phosphorylation system" in the context of a bacterial extract, refers to a bacterial extract that exhibits active oxidative phosphorylation during protein synthesis. For example, the bacterial extract can generate ATP using ATP synthase enzymes and reduction of oxygen driven by the oxidation of acetyl-CoA equivalents. It will be understood that other translation systems known in the art can also use an active oxidative phosphorylation during protein synthesis. The activation of oxidative phosphorylation can be demonstrated by inhibition of the pathway using specific inhibitors, such as electron transport chain inhibitors.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid or polynucleotide is used interchangeably with gene, cDNA, and mRNA encoded by a gene.

The term "nucleic acid template" refers to nucleic acid that encodes a protein, wherein the nucleic acid template is operably to produce the encoded protein upon contact with an *E. coli* derived cell free extract.

The term "naturally occurring amino acid" refers to any one of the 20 amino acids encoded by the genetic code, such as, (arginine, Arg, R; histidine, His, H; lysine, Lys, K; aspartic acid, Asp, D; glutamic acid, Glu, E; serine, S, Ser; threonine, Thr, T; asparagine, Asn, N; glutamine, Gln, Q; cysteine, Cys, G; glycine, Gly, G; proline, Pro, P; alanine, Ala, A; isoleucine, lie, I; leucine, Leu, L; methionine, Met, M; phenylalanine; Phe, F; tryptophan. Trp, W; tyrosine, Tyr, Y, and valine, Val, V, that are precursors to proteins.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used herein, the term "non-natural amino acid" refers to an amino acid that is not one of the 20 proteinogenic amino acids. Such non-natural amino acids can include, but are not limited to amino acids with side chains containing a sulfhydryl group; an azide group (e.g., azidohomoalanine or 5-para-azido-phenylalanine); an alkene group (3 homoallylglycine); an alkyne (2 homopropargylglycine); a ketone (4-para-acetyl-phenylalanine); or an aryl halide. In some cases, the non-natural amino acids allow site specific derivatization of the side-chain when incorporated into a protein chain. For example, a non-natural amino acid can be used to conjugate a protein to a linker, or a molecular payload. Methods and compositions for incorporating and using non-natural amino acids include, for example, those described in U.S. Patent Appl. Publ. Nos. 20140046030, and 20100184134; U.S. Pat. Nos. 8,715,958; and 8,778,631; Albayrak, C. and Swartz, J R., *Biochem. Biophys Res. Commun.*, 431(2):291-5; Yang W C et al., *Biotechnol. Prog.*, (2012), 28(2):413-20; Kuechenreuther et al., *PLoS One.* (2012), 7(9):e45850; and Swartz J R., *AIChE Journal,* 58(1):5-13, each of which are herein incorporated by reference in the entirety.

The phrase "codon encoding serine" refers to a nucleic acid triplet encoding the amino acid serine. There are six different codons (TCA, TCC, TCG, TCT, AGC and AGT) encoding serine.

The phrase "under conditions permitting the translation of the protein of interest" refers to a minimal condition (e.g., reaction components, time, temperature, etc.) needed for the producing of the protein of interest from a nucleic acid template encoding the protein.

The terms "polypeptide," "peptide" or "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "biologically active protein" refers to a protein that retains at least some of the biological activity of the protein of interest. The biological activity can be determined by comparing the activity, function and/or structure of the protein of interest expressed by the methods described herein to the activity of a reference protein of interest. For example, if the reference protein of interest is an IgG, a biologically active protein will comprise a properly folded and assembled IgG molecule. In some embodiments, the reference protein can be a protein expressed by a bacterial cell free synthesis system that does not contain an exogenous protein chaperone. The biological activity can be determined using an in vitro or in vivo assay that is appropriate for the protein of interest. The biological activity of the protein of interest can be expressed as the biological activity per unit volume of the cell-free protein synthesis reaction mixture. In some embodiments, the biological activity of a protein produced by the methods described herein is at least 30%, 40%, 50%, 60%, 70%, 80%, 90%, 95% or 99% of the activity of a reference protein.

The term "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies also include single chain antibodies (antibodies that exist as a single polypeptide chain), and single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988), *Proc. Nat. Acad. Sci. USA*, 85: 5879-5883. While the VH and VL are connected to each as a single polypeptide chain, the VH and VL domains associate non-covalently. The first functional antibody molecules to be expressed on the surface of filamentous phage were single-chain Fv's (scFv); however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see, e.g., U.S. Pat. Nos. 5,091,513; 5,132,405; and 4,956,778). Antibodies also include all those that have been displayed on phage (e.g., scFv, Fv, Fab and disulfide linked Fv (Reiter et al. (1995), *Protein Eng.*, 8: 1323-1331). Antibodies can also include diantibodies, miniantibodies and scFv-Fc fusions.

As used herein, the term "Fab fragment" is an antibody fragment that contains the portion of the full-length antibody that results from digestion of a full-length immunoglobulin with papain, or a fragment having the same structure that is produced synthetically, e.g. recombinantly. A Fab fragment contains a light chain (containing a variable ($V_L$) and constant ($C_L$) region domain) and another chain containing a variable domain of a heavy chain ($V_H$) and one constant region domain portion of the heavy chain ($C_{R1}$).

As used herein, a F(ab')$_2$ fragment is an antibody fragment that results from digestion of an immunoglobulin with pepsin at pH 4.0-4.5, or a synthetically, e.g. recombinantly, produced antibody having the same structure. The F(ab')$_2$ fragment contains two Fab fragments but where each heavy chain portion contains an additional few amino acids, including cysteine residues that form disulfide linkages joining the two fragments.

II. Detailed Description of Embodiments

Provided herein are methods for making a protein of interest that contains no detectable erroneous serine to asparagine substitutions. Such proteins of interest include antibodies and other recombinant proteins that are suitable for biological uses, such as therapeutic applications. The methods described herein provide a solution to the problem of serine to asparagine substitutions due to a 3/U mismatch. Such methods include codon optimizing a nucleic acid template encoding a serine containing protein and producing such a protein by cell free protein synthesis. Optionally, the protein of interest can contain one or more non-native amino acids.

As described herein, it was discovered that unintended amino acid substitutions of asparagine residues at serine positions can be avoided if a serine containing protein is produced in a cell free protein synthesis reaction that uses a nucleic acid template having no AGC codons. Furthermore, recombinant proteins of interest made using such a method exhibited increased fidelity. Surprisingly, the method also produced at higher protein titers. In fact, a 6-7 fold decrease in proteolysis or aborted product was observed when synthesizing proteins from a template with no AGC codons. In some instances, the method generated at least about 30% more protein compared to reactions using a similar template containing AGC codons.

A. General Methods

Unless defined otherwise, all technical and scientific terms used herein have the meaning commonly understood by one of ordinary skill in the art to which this invention belongs. Practitioners are particularly directed to Green, M. R., and Sambrook, J., eds., Molecular Cloning: A Laboratory Manual, 4th ed., Cold Spring Harbor Laboratory Press, Cold Spring Harbor, N.Y. (2012), and Ausubel, F. M., et al., Current Protocols in Molecular Biology (Supplement 99), John Wiley & Sons, New York (2012), which are herein incorporated by reference, for definitions and terms of the art. Standard methods also appear in Bindereif, Schón, & Westhof (2005) Handbook of RNA Biochemistry, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Green. M. R., and Sambrook. J., (Id.); Ausubel, F. M., et al., (Id.); Berger and Kimmel, Guide to Molecular Cloning Techniques, Methods in Enzymology (Volume 152 Academic Press, Inc., San Diego, Calif. 1987); and PCR Protocols: A Guide to Methods and Applications (Academic Press, San Diego, Calif. 1990), which are incorporated by reference herein.

Methods for protein purification, chromatography, electrophoresis, centrifugation, and crystallization are described in Coligan et al. (2000) Current Protocols in Protein Science, Vol. 1, John Wiley and Sons, Inc., New York. Methods for cell-free synthesis are described in Spirin & Swartz (2008) Cell-free Protein Synthesis, Wiley-VCH, Weinheim, Germany. Methods for incorporation of non-natural amino acids into proteins using cell-free synthesis are described in Shimizu et al (2006) FEBS Journal, 273, 4133-4140.

PCR amplification methods are well known in the art and are described, for example, in Innis et al., PCR Protocols: A Guide to Methods and Applications, Academic Press Inc. San Diego, Calif., 1990. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al., Short Protocols in Molecular Biology, 5th Edition, Wiley, 2002, and Innis et al., PCR Protocols, Academic Press, 990. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al., *Proc. Natl. Acad. Sci U.S.A.* 87:1663-1667, 1990; Eberwine et al., *Proc. Natl. Acad. Sci. U.S.A.* 89:3010-3014, 1992).

Unless defined otherwise, all technical and scientific terms used herein have the meaning commonly understood by one of ordinary skill in the art to which this invention belongs. Practitioners are particularly directed to Green, M. R., and Sambrook, J., eds., Molecular Cloning: A Laboratory Manual, 4th ed., Cold Spring Harbor Laboratory Press, Cold Spring Harbor, N.Y. (2012), and Ausubel, F. M., et al., Current Protocols in Molecular Biology (Supplement 99), John Wiley & Sons, New York (2012), which are incorporated herein by reference, for definitions and terms of the art. Standard methods also appear in Bindereif, Schón, & Westhof (2005) Handbook of RNA Biochemistry, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Green, M. R., and Sambrook, J., (Id.); Ausubel, F. M., et al., (Id.); Berger and Kimmel, Guide to Molecular Cloning Techniques, Methods in Enzymology (Volume 152 Academic Press, Inc., San Diego, Calif. 1987); and PCR Protocols: A Guide to Methods and Applications (Academic Press, San Diego, Calif. 1990), which are incorporated by reference herein.

Methods for protein purification, chromatography, electrophoresis, centrifugation, and crystallization are described in Coligan et al. (2000), Current Protocols in Protein Science, Vol. 1, John Wiley and Sons, Inc., New York. Methods for cell-free synthesis are described in Spirin & Swartz (2008) Cell-free Protein Synthesis, Wiley-VCH, Weinheim, Germany. Methods for incorporation of non-natural amino acids into proteins using cell-free synthesis are described in Shimizu et al (2006), *FEBS Journal,* 273, 4133-4140.

B. Introducing Serine Optimized Codons into Nucleic Acid Templates

The amino acid serine (Ser or S) is one of the most abundant amino acid in proteins such as antibodies. Serine can be encoded by 6 different codons, e.g., AGC, AGT, TCA, TCC, TCG, and TCT. The AGC codon is the most frequently used serine codon in monoclonal antibodies with about 35% to over 50% of all serines (Yu et al., *Anal Chem,* 2009, 81:9282-9290). For example, over 60% of the Ser residues in the antibody trastuzumab are AGC codons. During protein synthesis, translation errors can occur. These errors can introduce amino acid misincorporations and produce heterogeneous populations of recombinant proteins. For instance, recombinant monoclonal antibodies generated in mammalian cell lines can mistakenly incorporate asparagine (Asn or N) residues at serine positions, in particular, AGC codons. See, e.g., Yu et al., *Anal Chem,* 2009, 81:9282-9290.

To minimize Ser to Asn substitutions in a protein of interest, the nucleic acid template encoding the protein can be modified (mutated) such that all or substantially all of the AGC codons are reduced or eliminated, and replaced with either an AGT, TCG, TCA, TCT or TCC codon. In some embodiments, the serine codons AGT, TCG, TCA, TCT or TCC are approximately evenly distributed at the serine positions of the protein. In some embodiments, the serine codons TCG, TCA, TCT or TCC are approximately evenly distributed at the serine positions of the protein.

The codon optimized nucleic acid template encoding the protein of interest can have more than one serine residue. Said codon optimized template can include codons encoding serine wherein no more than 10%, e.g., 10%, 9%, 8%, 7%, 6%, 5%, 4%, 3%, 2%, 1%, or 0% of the codons encoding the serine residues are AGC. In some embodiments, the nucleic acid template contains no AGC codons. In some embodiments, the nucleic acid template contains no AGT codons. In other embodiments, the nucleic acid template contains no AGC codons and no AGT codons.

The nucleic acid template encoding the protein of interest can include serine codons such that about 20% to about 30%, e.g., about 20%, about 21%, about 22%, about 23%, about 24%, about 25%, about 26%, about 27%, about 28%, about 29% or about 30%, of the serine codons are TCG. The nucleic acid template encoding the protein of interest can include serine codons such that about 20% to about 30%, e.g., about 20%, about 21%, about 22%, about 23%, about 24%, about 25%, about 26%, about 27%, about 28%, about 29% or about 30%, of the serine codons are TCA. The nucleic acid template encoding the protein of interest can include serine codons such that about 20% to about 30%, e.g., about 20%, about 21%, about 22%, about 23%, about 24%, about 25%, about 26%, about 27%, about 28%, about 29% or about 30%0, of the serine codons are TCT. The nucleic acid template encoding the protein of interest can include serine codons such that about 20% to about 30%, e.g., about 20%, about 21%, about 22%, about 23%, about 24%, about 25%, about 26%, about 27%, about 28%, about 29% or about 30%, of the serine codons are TCC. The nucleic acid template encoding the protein of interest can include serine codons such that about 20% to about 30%, e.g., about 20%, about 21%, about 22%, about 23%, about 24%, about 25%, about 26%, about 27%, about 28%, about 29% or about 30%, of the serine codons are AGT. In some embodiments, nucleic acid template includes no AGT codons.

The serine codons of wild-type nucleic acid template encoding the protein can be modified using standard molecular techniques recognized by those of ordinary skill in the art. Such methods include, but are not limited to, PCR, mutagenesis, and restriction enzyme cloning. Molecular cloning techniques are described in detail in, for example, *Molecular Cloning: A Laboratory Manual,* 4th ed., Cold Spring Harbor Laboratory Press, Cold Spring Harbor, N.Y.

(2012); Ausubel, F. M., et al., *Current Protocols in Molecular Biology* (Supplement 99), John Wiley & Sons, New York (2012); Berger and Kimmel, *Guide to Molecular Cloning Techniques, Methods in Enzymology* (Volume 152 Academic Press, Inc., San Diego, Calif. 1987); and *PCR Protocols: A Guide to Methods and Applications* (Academic Press, San Diego, Calif. 1990). Optionally, the serine codon optimized template can be produced using synthetic chemistry according to standard methods, e.g., the solid phase phosphoramidite triester method.

It is recognized by those skilled in the art that various well-known mutagenesis techniques are available to generate the codon optimized template of this invention. For instance, point mutations corresponding to the desired serine codon described herein can be introduced by overlapping PCR. Optionally, the wild-type coding sequence can be mutated using a PCR-based mutagenesis technique, e.g., site-directed mutagenesis, to mutate the AGC codons and introduce the AGT, TCG, TCA, TCT and/or TCC codons.

More specifically such mutagenesis techniques include, e.g., site-directed mutagenesis (e.g., QuikchangeII™ Site Directed Mutagenesis kit, Agilent Technologies), random mutagenesis (Diversify™ PCR Random Mutagenesis Kit, Clontech), homologous recombinations, oligonucleotide-directed mutagenesis (e.g., Transformer™ Kit, Clontech), phosphorothioate-modified DNA mutagenesis, etc., can be used to generate a coding sequence corresponding to amino acid substitutions. See, e.g., Ling, et al., "Approaches to DNA mutagenesis: an overview," *Anal. Biochem.*, 254(2): 157-78 (1997); Dale, et al., "Oligonucleotide-directed random mutagenesis using the phosphorothioate method," *Methods Mol. Biol.*, 57:369-74 (1996); Smith, "In vitro mutagenesis," *Ann. Rev. Genet.*, 19:423-462 (1985); Botstein, et al., "Strategies and applications of in vitro mutagenesis," *Science*, 229:1193-1201 (1985); Carter, "Site-directed mutagenesis," *Biochem. J.*, 237:1-7 (1986); Kramer, et al., "Point Mismatch Repair," *Cell*, 38:879-887 (1984); Wells, et al., "Cassette mutagenesis: an efficient method for generation of multiple mutations at defined sites," *Gene*, 34:315-323 (1985); Minshull, et al., "Protein evolution by molecular breeding." *Current Opinion in Chemical Biology*, 3:284-290 (1999); Christians, et al., "Directed evolution of thymidine kinase for AZT phosphorylation using DNA family shuffling," *Nature Biotechnology*, 17:259-264 (1999); Crameri, et al., "DNA shuffling of a family of genes from diverse species accelerates directed evolution," *Nature*, 391:288-291; Crameri, et al., "Molecular evolution of an arsenate detoxification pathway by DNA shuffling," *Nature Biotechnology*, 15:436-438 (1997); Zhang, et al., "Directed evolution of an effective fucosidase from a galactosidase by DNA shuffling and screening," *Proceedings of the National Academy of Sciences, U.S.A.*, 94:45-4-4509; Crameri, et al., "Improved green fluorescent protein by molecular evolution using DNA shuffling," *Nature Biotechnology*, 14:315-319 (1996); Stemmer, "Rapid evolution of a protein in vitro by DNA shuffling," *Nature*, 370:389-391 (1994); Stemmer, "DNA shuffling by random fragmentation and reassembly: In vitro recombination," *Proceedings of the National Academy of Sciences, U.S.A.*, 91:10747-10751 (1994); WO95022625; WO97035966; WO98027230; WO00042651; WO01075767; and WO2009152336, all of which are incorporated herein by reference. Kits and reagents are commercially available from, e.g., SIGMA-ALDRICH (Saint Louis, Mo.), R&D systems (Minneapolis, Minn.), Pharmacia LKB Biotechnology (Piscataway, N.J.), Clontech Laboratories, Inc. (Palo Alto, Calif.), Bio-Rad Laboratories (Hercules, Calif.), Life Technologies (Carlsbad, Calif.), Applied Biosystems (Fosters City, Calif.), Roche Diagnostics (Indianapolis, Ind.), as well as many other sources known to one of skill in the art.

The nucleic acid template can be operably linked to at least one promoter and to one or more other regulatory sequences including without limitation repressors, activators, transcription and translation enhancers, DNA-binding proteins, etc. Suitable quantities of DNA template for use herein can be produced by amplifying the DNA in well-known cloning vectors and hosts, or by polymerase chain reaction (PCR). The template can be introduced into an expression vector or plasmid for expression in a host cell such as a bacterial cell.

Non-limiting examples of a protein of interest include an antibody, antibody fragment, anti-idiotype antibody, chimeric antibody, humanized antibody, antibody fusion protein, secreted protein (e.g., hormone), transmembrane protein (e.g., receptor), enzyme, proprotein, protein fragment, pharmaceutically active protein, protein with one or more disulfide bonds, protein having at least two proline residues, growth factors, receptors, cytokines, enzymes, ligands, and protein having a potential industrial or therapeutic value. In some embodiments, the protein of interest is an antibody or an antibody fragment. Non-limiting examples of an antibody include an immunoglobulin such as IgA, e.g., $IgA_1$ and $IgA_2$, IgD, IgE, IgM, IgG, e.g., $IgG_1$, $IgG_2$, $IgG_3$, and $IgG_4$, a humanized antibody, chimeric antibody, anti-idiotype antibody, monoclonal antibody, polyclonal antibody, or therapeutic antibody, and the like. Non-limiting examples of an antibody fragment include a monovalent antibody fragment such as a fragment having a single antigen binding arm and an Fc region, Fab molecule, Fab' molecule, Fab'-SH molecule, $F(ab')_2$ fragment, Fv molecule, diabody, single-chain antibody fragment, single-chain Fv (scFv) molecules, and the like.

The protein of interest can contain one or more non-natural (non-native) amino acid. Detailed descriptions of methods for generating a protein containing a non-natural amino acid is described in Zimmerman et al., *Bioconjugate Chem*, 2014, 25:351-361, International Application Publication Nos. WO02015054590, and WO2015054587, U.S. Patent Application Publication No. 2015017187, and U.S. Pat. No. 8,778,631, the disclosures of which are herein incorporated by reference in their entirety for all purposes.

C. Generating Proteins Using Cell Free Protein Synthesis

Once the desired nucleic acid template is obtain, it can be used to generate the corresponding polypeptide in a cell free protein synthesis system. Such protein synthesis systems include, but are not limited to, one or more bacterial extracts, at least ATP or an energy source (e.g., pyruvate, glucose and glutamate), co-factors, enzymes and other reagents that are necessary for polypeptide synthesis, e.g., ribosomes, tRNA, folinic acid, polyamines, polymerases, transcriptional factors, aminoacyl synthetases, chaperones, elongation factors, initiation factors, etc.

Detailed descriptions of suitable cell free protein synthesis systems and methods are found in, e.g., Cai et al., *Biotechnol Prog*, 2015, doi: 10.1002/btpr.2082; U.S. Pat. Nos. 9,040,253; 8,778,631; U.S. Application Publication Nos. 20100184134; 20100203587; 2015259664; 2015017187 and PCT Application Publication Nos. WO2015054658; WO2014176327; and WO2014176439, their disclosures are herein incorporated by reference in their entirety for all purposes. In some embodiments, proteins encoded by serine codon optimized templates are generated using Sutro Biopharma's Xpress CF™ platform and Xpress CF+™ platform.

In some embodiments, the protein of interest is produced at a concentration (e.g., level or amount) greater than 6 mg/liter, e.g., 7 mg/liter, 8 mg/liter, 9 mg/liter, 10 mg/liter, 11 mg/liter, 12 mg/liter, 13 mg/liter, 14 mg/liter, 15 mg/liter, 16 mg/liter, 17 mg/liter, 18 mg/liter, 19 mg/liter, 20 mg/liter, 21 mg/liter, 22 mg/liter, 23 mg/liter, 24 mg/liter, 25 mg/liter, 30 mg/liter, 40 mg/liter, 50 mg/liter, 60 mg/liter, 70 mg/liter, 80 mg/liter, 90 mg/liter, 100 mg/liter, 200 mg/liter, 300 mg/liter, 400 mg/liter, 500 mg/liter, 600 mg/liter, 700 mg/liter, 800 mg/liter, 900 mg/liter, 1000 mg/liter, or more. In other embodiments, the concentration (e.g., level or amount) is 500 mg/liter or greater, e.g., 500 mg/liter, 600 mg/liter, 700 mg/liter, 800 mg/liter, 900 mg/liter, 1000 mg/liter, 1100 mg/liter, 1200 mg/liter, 1300) mg/liter, 1400 mg/liter, 1500 mg/liter, 1600 mg/liter, 1700 mg/liter, 1800 mg/liter, 1900 mg/liter, 2000 mg/liter, or more. In some instances, the concentration (e.g., level or amount) is greater than 1000 mg/liter, 1100 mg/liter, 1200 mg/liter, 1300 mg/liter, 1400 mg/liter, 1500 mg/liter, 1600 mg/liter, 1700 mg/liter, 1800 mg/liter, 1900 mg/liter, 2000 mg/liter, or more.

In some embodiments, the protein of interest contains amino acids wherein more than 15%, e.g., 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69% or more of the amino acids are serine residues. The proteins of interest can contain about 16% to 50% serine resides, 20% to 60% serine residues, 30% to 70% serine residues, about 16% to 30% serine resides, about 20% to 40% serine resides, about 25% to 50% serine resides, about 40% to 60% serine resides, about 16% to 18% serine resides, about 16% to 25% serine resides, and the like.

In some embodiments, the wild-type (e.g., original or reference) protein of interest contains amino acids wherein more than 15%, e.g., 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80% or more of the serine codons are AGC. If the protein of interest is generated using the compositions or methods described herein, the synthesized protein will contain amino acids wherein 10% or less, e.g., 10%, 9%, 8%, 7%, 6%, 5%, 4%, 3%, 2%, 1% or less of the serine codons are AGC. In some embodiments, the synthesized protein contains no AGC codons.

1. Culturing Bacteria for Making a Cell Free Extract

Bacteria, e.g., *E. coli* can be provided for forming a cell free extract. Typically, bacteria are cultured from a stock or starter culture to obtain sufficient biomass. Bacterial culturing is well known to those skilled in the art. A bacterial lysate derived from any strain of bacteria can be used in the methods of the invention. Bacteria suitable for use in cell free synthesis systems include gram-negative bacteria and gram-positive bacteria, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, and *Pseudomonas* such as *P. aeruginsa*, and *Steptomyces*. In preferred embodiments, the bacteria used in the formulations and methods provided herein are from an *Escherichia* species, such as *Escherichia coli* or a derivative thereof.

The bacterial strain used to make the cell extract may have reduced nuclease and/or phosphatase activity which increases cell free synthesis efficiency. For example, the bacterial strain used to make the cell free extract can have mutations in the genes encoding the nucleases RNase E and RNase A. The strain may also have mutations to stabilize components of the cell synthesis reaction such as deletions in genes such as tnaA, speA, sdaA or gshA, which prevent degradation of the amino acids tryptophan, arginine, serine and cysteine, respectively, in a cell-free synthesis reaction. Additionally, the strain may have mutations to stabilize the protein products of cell-free synthesis such as knockouts in the proteases ompT or lonP.

Bacterial cells can be transfected or transformed with expression or cloning vectors and cultured in conventional nutrient media modified as appropriate for inducing promoters, selecting transformations and preparing bacterial extracts, as described herein.

The bacterial culture can be obtained as follows. The bacteria of choice are grown up overnight in any of a number of growth media and under growth conditions that are well known in the art and easily optimized by a practitioner for growth of the particular bacteria. In general, isolated strains of bacteria are grown in media until they reach balanced exponential growth phase or stationary phase. This can be between $10^6$ to $10^9$ cells per mL. In some embodiments, the culture is harvested when the pH of the culture rises above a set point indicating the depletion of glucose in the media. The bacterial culture can be grown to an $OD_{595-600}$ of 10 to 60, depending on the bacterial strain used. In some embodiments, the bacteria is cultured at a growth rate of about 0.06 to about 0.6 to about 0.8 doublings per hour.

When large amounts of bacteria are needed, continuous culturing means are employed instead of batch systems which are closed. These continuous systems involve the continued introduction of nutrients and removal of waste. Optimally, this permits the cells to be grown at a constant biomass concentration for extended periods. Two well-known systems are chemostats and turbidostats. In the chemostat system sterile media is fed in at a constant rate while media containing bacteria is removed at the same rate. The turbidostat system uses a photocell to measure absorbance or turbidity and regulates the inflow of sterile media and outflow of bacteria according to preset signals.

Methods of culturing bacteria are described in, e.g., Zawada et al., *Biotechnol. Bioeng.*, 2011, 108(7):1570-1578; Zawada, J. "Preparation and Testing of *E. coli* S30 In Vitro Transcription Translation Extracts", Douthwaite, J. A. and Jackson, R. H. (eds.), Ribosome Display and Related Technologies: Methods and Protocols, Methods in Molecular Biology, vol. 805, pp. 31-41 (Humana Press, 2012); Jewett et al., *Molecular Systems Biology*, 2008, 4, 1-10; Shin J. and Norieaux V., *J. Biol. Eng.*, 2010, 4:8.

2. Preparing Bacterial Extracts

Once the bacterial culture is ready for harvest, it can be cooled to 2-8° C., usually on ice or through heat exchangers when the culture is of a large scale. The culture can be centrifuged to separate the spent media from the cell paste (cell slurry). Preferred centrifuges include disk stack centrifuges, tubular bowl centrifuges, and other centrifuges for large or small scale bacterial cultures. The cell paste is typically resuspended in S30 buffer, any equivalent buffer solution, or water. S30 buffer comprises 10 mM Tris acetate, 14 mM magnesium acetate and 60 mM potassium acetate. In some embodiments, a 1:1, 2:1, 3:1, 4:1, 5:1, 6:1, 7:1, 8:1 or more dilution (liquid:solid; ml of buffer:gram weight of cells) is made for washing. The cell paste can be washed again in S30 buffer or any equivalent buffer, and centrifuged to remove any residual buffer. For small scale cultures, a second wash step is typically performed. At washing the cell paste (cell pellet) can be stored at −80° C. for use later or further processed by homogenization to lyse the cells.

A cell extract can be prepared from cultured bacteria, as described above. Cells that have been fermented overnight can be lysed by suspending the cell pellet in a suitable cell suspension buffer, and disrupting the suspended cells by sonication, breaking the suspended cells in a French press or with glass beads, continuous flow high pressure homogenization, or any other method known in the art useful for efficient cell lysis. The cell lysate is then centrifuged or filtered to remove large cell debris, including DNA, and cells that have not been lysed.

In some embodiments, the bacterial culture is pelleted by centrifugation at greater than 14,000×g for about 45 min at about 8-20° C. twice in a tubular bowl centrifuge in continuous or batch mode or a disc stack continuous centrifuge with a maximum bowl speed of about 12,000 rpm and a feed flow rate of about 3.0-3.3 L/min. The pelleted cells are resuspended and repelleted with S30 buffer. In some embodiments, the cells are stored at −80° C. for use later or processed by homogenization.

Prior to homogenization, the cell pellet can be resuspended in S30 buffer or an equivalent to produce a cell suspension. In some embodiments, a 1:1, 2:1, 3:1, 4:1, 5:1, 6:1, 7:1, 8:1 or more dilution (liquid:solid; ml of buffer:gram weight of cells) is created. Preferably, a 2:1 dilution is made such that 2 ml of S30 buffer is used per gram weight of cell pellet.

The cell suspension can be homogenized or disrupted in a standard high pressure homogenizer (e.g., an Avestin Emulsiflex C-55a Homogenizer) and/or microfluidizer (e.g., Microfluidics Microfluidizer) set at the appropriate pressure, such as 3,000 psi to produce a lysate. The homogenization step lyses the bacteria to release the necessary components required for protein synthesis, and in some aspects, formed inverted membrane vesicles provide energy for protein synthesis via respiration.

The extract can be filtered through one or more sterilizing grade filter membranes. e.g., a 0.45 µm filter membrane and/or a 0.22 µm filter membrane. A 0.45 m filter membrane can be used first, and then a 0.22 µm filter membrane afterwards.

In some embodiments, the filtered extract is activated or pre-incubated at 30° C. for about 2-5 hours, preferably for about 2.5 hours. After pre-incubation, particulates from the extract can be separated by centrifugation, e.g., spinning at least 14,000×g for about 35 minutes.

The lysed bacterial extract can be aliquoted and frozen in liquid nitrogen before storing at −80° C. Optionally, a cell free synthesis reaction mix, as described herein, can be added to the cell free extract prior to freezing.

Methods of preparing a lysed bacterial extract are described in, e.g., Zawada, J. "Preparation and Testing of *E. coli* S30 In Vitro Transcription Translation Extracts", Douthwaite, J. A. and Jackson, R. H. (eds.), *Ribosome Display and Related Technologies: Methods and Protocols, Methods in Molecular Biology*, vol. 805, pp. 31-41 (Humana Press, 2012); Jewett et al., *Molecular Systems Biology*, 2008, 4, 1-10; and Shin J. and Norieaux V., *J. Biol. Eng.*, 2010, 4:8.

3. Cell Free Protein Synthesis Reactions

Biologically active proteins of interest can be synthesized, properly folded and/or assembled using a cell free protein synthesis (CFPS) system such as an *Escherichia coli*-based cell-free system, including an open cell free system (OCFS). CFPS systems have been used to generate various proteins including growth factors (Zawada et al., *Biotechnol Bioeng*, 108:1570-1578 (2011)), full-length antibodies and antibody fragments (Yin et al., *mAbs*, 4(2):217-225 (2012)) and antibody-drug conjugates (Zimmerman et al., *Bioconjug Chem*, 25(2):351-61 (2014)). Detailed descriptions of cell free protein synthesis systems are found in, for example, Cai et al., *Biotechnol Prog*, 2015, doi: 10.1002/btpr.2082 and U.S. Pat. Nos. 7,338,879; 8,183,010 and 8,492,115, the disclosures of which are herein incorporated by reference in their entirety for all purposes.

A CFPS reaction mixture can contain the following components: a template nucleic acid, such as DNA, that comprises a gene of interest operably linked to at least one promoter and, optionally, one or more other regulatory sequences (e.g., a cloning or expression vector containing the gene of interest) or a PCR fragment; an RNA polymerase that recognizes the promoter(s) to which the gene of interest is operably linked (e.g. T7 RNA polymerase) and, optionally, one or more transcription factors directed to an optional regulatory sequence to which the template nucleic acid is operably linked; ribonucleotide triphosphates (rNTPs); optionally, other transcription factors and co-factors therefor; ribosomes; transfer RNA (tRNA); other or optional translation factors (e.g., translation initiation, elongation and termination factors) and co-factors therefore; one or more energy sources, (e.g., ATP, GTP); optionally, one or more energy regenerating components (e.g., PEP/pyruvate kinase, AP/acetate kinase or creatine phosphate/creatine kinase); optionally factors that enhance yield and/or efficiency (e.g., nucleases, nuclease inhibitors, protein stabilizers, chaperones) and co-factors therefore; and; optionally, solubilizing agents. The reaction mix can also include amino acids and other materials specifically required for protein synthesis, including salts (e.g., potassium, magnesium, ammonium, and manganese salts of acetic acid, glutamic acid, or sulfuric acids), polymeric compounds (e.g., polyethylene glycol, dextran, diethyl aminoethyl dextran, quaternary aminoethyl and aminoethyl dextran, etc.), cyclic AMP, inhibitors of protein or nucleic acid degrading enzymes, inhibitors or regulators of protein synthesis, oxidation/reduction adjuster (e.g., DTT, ascorbic acid, glutathione, and/or their oxides), non-denaturing surfactants (e.g., Triton X-100), buffer components, spermine, spermidine, putrescine, etc. Components of such reactions are discussed in more detail in U.S. Pat. Nos. 7,338,789; 7,351,563; 8,715,958; and 8,778,631, the disclosures of each are incorporated by reference in their entirety for all purposes.

Depending on the specific enzymes present in the extract, for example, one or more of the many known nuclease, polymerase or phosphatase inhibitors can be selected and advantageously used to improve synthesis efficiency.

Protein and nucleic acid synthesis typically requires an energy source. Energy is required for initiation of transcription to produce mRNA (e.g., when a DNA template is used and for initiation of translation high energy phosphate for example in the form of GTP is used). Each subsequent step of one codon by the ribosome (three nucleotides; one amino acid) requires hydrolysis of an additional GTP to GDP. ATP is also typically required. For an amino acid to be polymerized during protein synthesis, it must first be activated. Significant quantities of energy from high energy phosphate bonds are thus required for protein and/or nucleic acid synthesis to proceed. In some embodiments, the cell-free synthesis reaction does not require the addition of common secondary energy sources, yet uses co-activation of oxidative phosphorylation and protein synthesis.

In some instances, CFPS is performed in a reaction such as the Cytomim™ (cytoplasm mimic) system which utilizes an active oxidative phosphorylation system. The Cytomim™ system includes a reaction condition performed in the absence of polyethylene glycol with optimized magnesium concentration. This system does not accumulate phosphate, which is known to inhibit protein synthesis. Detailed descriptions of the Cytomim™ system are found in, for example, U.S. Pat. No. 7,338,789; Jewett et al., *Mol Syst Biol*, 2008, 4:220; Spirin, A. S. and Swartz, J. R. (2008) *Cell-free Protein Synthesis; Methods and Protocols*, New Jersey: John Wiley & Sons, the contents are herein incorporated by reference in their entirety for all purposes.

D. Methods for Detecting Amino Acid substitutions in Proteins

The proteins produced by the methods described above can be analyzed for translational fidelity. Prior to analysis the proteins can be purified by, for example, affinity chromatography, hydrophobic interaction chromatography, size exclusion chromatography, and the like. See, e.g., Yin et al., mAbs, 2012, 4(2):217-225. Amino acid substitutions in proteins can be detected using methods such as, but not limited to, electrophoresis-based assays, e.g., isoelectric focusing and two-dimensional gel electrophoresis, sequencing assays, e.g., Edman sequencing, chromatography, e.g., ion-exchange chromatography, HPLC, and reversed-phase HPLC, and mass spectrometry (MS), e.g., liquid chromatography-tandem mass spectrometry (LC-MS/MS).

Peptide mapping by mass spectrometry including LC-MS/MS is highly sensitive, selective, and accurate. See, e.g., Zimmerman et al., *Bioconjugate Chem*, 2014, 25:351-361. This method allows for the analysis of mixed population of proteins such as misincorporated proteins and properly incorporated proteins, thereby eliminating the need of isolating the error-prone proteins. Data analysis software packages, e.g., Mascot based error tolerant search (ETS) and SIEVE can also be used to detect a low level of sequence variants in a mixed population of proteins (Zeck et al., *PLoS One*, 2012, 7(7):e40328).

The presence and location of specific amino acid changes can be detected using enzymatic digestions such as, but not limited to, tryptic, chymotryptic and restriction enzyme digestions in combination with mass spectrometry. See, e.g., Huang et al., *Protein Sci*, 2012, 21(5):625-632; Que et al., *BioProcess International*, 2010, 8(8):52-60.

E. Methods for Measuring Protein Titers

The present invention is based, in part, on the unexpected and advantageous discovery that the elimination of Ser to Asn misincorporations by replacing AGC codons in a nucleic acid template encoding a protein of interest can significantly increase protein yield in cell free protein synthesis.

The proteins produced by the methods described above can be analyzed to determine protein yield (titer). Standard methods can be used to determine protein titer such as, but not limited to, SDS-PAGE, western blotting, chromatography, e.g., analytical size exclusion chromatography, liquid chromatography and HPLC, immuno-based assays, and enzyme-linked immunosorbent assays (ELISAs).

Protein yield from CFPS can be quantified by the incorporation of radioactive amino acids, such as, but not limited to, $C^{14}$-leucine, $C^{14}$-phenylalanine, $C^{14}$-alanine, $C^{14}$-glycine, $C^{14}$-valine, and the like. Following the protein synthesis reaction, the resulting radioactive reaction products can be spotted on a filter membrane and precipitated with 10% trichloroacetic acid. Afterwards, the membranes can be washed. The radioactivity can be measured in a gas-flow counter or a liquid scintillation counter.

III. Examples

The following examples are offered to illustrate, but not to limit, the claimed invention.

Example 1. Generating Serine Codon Optimized Antibody Heavy Chain (HC) and Light Chain (LC) Nucleic Acid Templates for an Anti-CD74 Antibody Codon usage analysis showed that greater than 60% of serine codons in the nucleic acid encoding an anti-CD74 heavy chain or light chain were AGC. The AGC codon can potentially causes serine to asparagine (S to N) substitutions due to a G/U mismatch at the second base pair of the codon. To eliminate such an amino acid substitution, the wild-type template was modified to replace all the AGC codons and evenly distribute other serine codons, such as TCG, TCA, TCT and TCC (FIG. 1). Thus, the serine optimized template encoding the anti-CD74 heavy and light chain contained no AGT (rare codon) and AGC codons, and about 25% (e.g., about 23-27%) of each of the TCG, TCA, TCT and TCC codons.

Wild-type genes (DNA) coding for anti-CD74 heavy chain and light chain ("original sequence" or "v1") and serine codon optimized heavy chain and light chain ("optimized sequence" or "v2") genes were synthesized (DNA 2.0, Menlo Park, Calif.). The only difference between v1 and v2 was serine codon usage.

The wild-type anti-CD74 heavy chain nucleic acid template contained 34 AGC codons (about 65% of the total serine codons were AGC), 3 TCG codons, 1 TCA codon, 6 TCT codons, 9 TCC codons and no AGT codons (FIG. 1). The wild-type anti-CD74 light chain nucleic acid template had 20 AGC codons, 2 TCG codons, 1 TCA codons, 2 TCT codons, 4 TCC codons and no AGT codons.

In contrast, the codon optimized anti-CD74 heavy chain gene included no AGC or AGT codons, 13 TCG codons, 13 TCA codons, 14 TCT codons, and 12 TCC codons. The codon optimized light chain contained no AGC or AGT codons, 8 TCG codons, 7 TCA codons, 7 TCT codons and 8 TCC codons (FIG. 1).

Example 2. Cell Free Protein Synthesis for Producing Antibodies with Codon Optimized Serines The nucleic acid templates encoding the anti-CD74 heavy chain and light chain as described in Example 1 were used in cell free protein synthesis to produce full-length IgG. The nucleic acid templates were co-expressed in the presence of disulfide isomerase chaperones DsbC or PDI. The added chaperones can facilitate the formation of disulfide bonds and promote proper folding and antibody assembly.

Briefly, the cell free protein synthesis reaction as described in Zawada et al., 2011, *Biotechnol. Bioeng.* 108 (7): 1570-1578 was performed with the following modifications. The cell-free extracts were prepared from an OmpT sensitive RF-1 attenuated strain that was also engineered to overexpress *E. coli* DsbC, and a similar RF-1 attenuated *E. coli* strain. The cell-free extracts were, treated with 50 μM iodoacetamide for 30 min at RT (20° C.), and then added to a premix containing all other components of a cell-free protein synthesis system except for the nucleic acid templates (DNA plasmids) encoding IgG heavy and light chains. The final concentration in the cell free protein synthesis reaction was 30% cell extract, 2 mM GSSG, 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for tyrosine and phenylalanine), 4 mM sodium oxalate, 1 mM putrescine, 1.5 mM spermidine, 15 mM potassium phosphate, 100 nM T7 RNAP, 2 µg/mL Ser codon-optimized trastuzumab light chain DNA, 8 µg/mL Ser codon-optimized trastuzumab-(His)6 heavy chain DNA. The cell-free synthesis reactions were initiated by the addition of the serine optimized plasmid DNA encoding the IgG heavy and light chain. The reactions were incubated at 30° C. for 12 h on a shaker at 650 rpm in 48-well Flower plates (m2p-labs # MTP-48-B). The reaction was incubated further at 4° C. for 6 h until it was processed for purification.

To quantify protein yield, the reaction mixture was supplemented with a small amount of $C^{14}$ labeled leucine (3 µL per 100 µL reaction, PerkinElmer: NEC279E001MC, 0.1 mCi/mL). A 4 µL aliquot of each reaction was spotted on a Filtermat A (PerkinElmer: 1450-421) before and after centrifugation at 6,100×g for 15 min and dried on a hot plate at 100° C. for 10 min. The Filtermat with supernatant samples was washed three times for 15 minutes with 5% trichloroacetic acid on ice to remove unincorporated $C^{14}$ leucine, rinsed with absolute ethanol and dried on the hot plate. The Filtermat with non-centrifuged samples was not washed. All Filtermats were coated with MeltiLex melt-in scintillate (PerkinElmer: 1450-441) and counted in a Wallac MicrobetaTrilux liquid scintillation and luminescence counter (model 1450). Soluble protein yield was calculated according to:

$$P_{sol} = [LEU]_{total} \times \frac{MW}{(\# LEU)} \times \frac{C_{sol}}{C_{full}}$$

where $P_{sol}$ is the soluble protein titer in mg/mL, $[Leu]_{total}$ is the total Leu concentration in the reaction (commonly 2 mM), $$\frac{MW}{(\# Leu)}$$

is the ratio of molecular weight to number of Leu in the proteins and $$\frac{C_{sol}}{C_{full}}$$

is the ratio of counts measured by the scintillation counter in the soluble fraction and full reaction mixture. For products with quaternary structure (scFvFc, IgG, Fab), autoradiograms were run using 4-12% Bis-Tris SDS-PAGE gels (Invitrogen) to determine assembly of the proper complex. Both reducing and non-reducing gels were run following the manufacturer's instructions. Exposed phosphor screens were scanned by Typhoon FLA 7000 (GE Healthcare life sciences) and the intensity of the bands was quantified by ImageQuant software (GE). The final yield of assembled complex was calculated according to the equation:

$$P_{complex} = P_{sol} \times I_{nr}^{complex} / \Sigma I_r$$

where $P_{complex}$ is the titer of the correctly assembled complex in mg/mL, $P_{sol}$ is the soluble protein titer, $I_{nr}^{complex}$ is the intensity of the correctly assembled complex band on the non-reducing gel and $\Sigma I_r$ is the sum of intensities of all bands on the reducing gel.

The protein yield from the serine codon nucleic acid template increased by 30% compared to the wild-type template (FIG. 2C). More IgG was assembled when the heavy chain to light chain ratio was 4:1 or 3:1. At a ratio of 2:1, there was no difference in the protein yield. The total IgG yield was also higher in CFPS reactions using the serine optimized templates for anti-CD74 antibodies (FIG. 2C). The maximal yield for anti-CD74 antibody was less than 700 mg/L when the ratio of wild-type heavy chain template to wild-type light chain template was 3:1. On the other hand, the maximal yield for anti-CD74 antibody was about 900 mg/L when the ratio of serine optimized heavy chain template to serine optimized light chain template was 4:1. The purified IgG was analyzed by SDS-PAGE followed by autoradiography (FIGS. 2A and 2B). Under reducing conditions (e.g., in the DTT), the serine optimized anti-CD74 was resolved into a heavy-chain band and a light-chain band. Notably, about 6-7 fold less proteolysis or prematurely terminated (e.g., aborted) protein product was generated from the codon optimized template compared to the wild-type plasmid.

Next the presence or absence of the serine to asparagine substitution in the anti-CD74 heavy chain and light chains was determined by mass spectrometry. Proteins were incubated in 4 M Gud HCl and 10 mM DTT for 30 minutes at 45° C., cool to room temperature, acidify and then store at 4-10° C. until the sample was run on the LC-MS. Mass spectra of proteins or antibody chains were deconvoluted using the Maximum Entropy potassium phosphate, 100 nM T7 RNAP, 2 µg/mL Ser-codon optimized anti-CD74 IgG light chain DNA, 8 µg/mL Ser-codon optimized anti-CD74 IgG light chain heavy chain DNA containing an amber codon at the F404 site. The cell-free synthesis reactions were initiated by the addition of the serine optimized plasmid DNAs encoding the IgG heavy and light chain. The reactions were incubated at 30° C. for 12 h on a shaker at 650 rpm in 48-well Flower plates (m2p-labs # MTP-48-B). The reaction was incubated further at 4° C. for 6 h until it was processed for purification.

Following the cell-free protein synthesis reaction, the mixture containing para-methylazido-L-phenylalanine containing antibodies was transferred to a 96-well plate (DyNa Block™, 2 mL; Labnet, Edison, N.J.) and centrifuged at 5000×g for 15 minutes at 40° C. Purification of IgG from the cell-free supernatant was carried out by using IMAC Phytips (Phynexus, San Jose, Calif.) containing 40 µL resin. The resin bed was pre-equilibrated in IMAC equilibration buffer (50 mM Tris pH 8.0, 300 mM NaCl, 10 mM imidazole) and the clarified supernatant was pipetted up and down 10 times through equilibrated IMAC Phytips at a flow rate of 4.2 µL/min. The bound protein was washed with IMAC equilibration buffer, and then eluted with 125 µL IMAC elution buffer (50 mM Tris pH 8.0, 300 mM NaCl, 500 mM imidazole).

To quantify protein yield, the reaction mixture was supplemented with a small amount of C-14 labeled leucine (3 µL per 100 µL reaction, PerkinElmer: NEC279E001MC, 0.1 mCi/mL). A 4 µL aliquot of each reaction was spotted on a Filtermat A (PerkinElmer: 1450-421) before and after centrifugation at 6,100×g for 15 min and dried on a hot plate at 100° C. for 10 min. The Filtermat with supernatant samples was washed three times for 15 minutes with 5% trichloroacetic acid on ice to remove unincorporated C-14 leucine, rinsed with absolute ethanol and dried on the hot plate. The Filtermat with non-centrifuged samples was not washed. All Filtermats were coated with MeltiLex melt-in scintillate (PerkinElmer: 1450-441) and counted in a Wallac MicrobetaTrilux liquid scintillation and luminescence counter (model 1450). Soluble protein yield was calculated according to:

$$P_{sol} = [LEU]_{total} \times \frac{MW}{(\# LEU)} \times \frac{C_{sol}}{C_{full}}$$

where $P_{sol}$ is the soluble protein titer in mg/mL, $[Leu]_{total}$ is the total Leu concentration in the reaction (commonly 2 mM), $$\frac{MW}{(\# Leu)}$$

is the ratio of molecular weight to number of Leu in the proteins and $$\frac{C_{sol}}{C_{full}}$$

is the ratio of counts measured by the scintillation counter in the soluble fraction and full reaction mixture. For products with quaternary structure (scFvFc, IgG, Fab), autoradiograms were run using 4-12% Bis-Tris SDS-PAGE gels (Invitrogen) to determine assembly of the proper complex. Both reducing and non-reducing gels were run following the manufacturer's instructions. Exposed phosphor screens were scanned by Typhoon FLA 7000 (GE Healthcare life sciences) and the intensity of the bands was quantified by ImageQuant software (GE). The final yield of assembled complex was calculated according to the equation:

$$P_{complex} = P_{sol} \times I_{nr}^{complex} / \Sigma I_r$$

where $P_{complex}$ is the titer of the correctly assembled complex in mg/mL, $P_{sol}$ is the soluble protein titer, $I_{nr}^{complex}$ is the intensity of the correctly assembled complex band on the non-reducing gel and $\Sigma I_r$ is the sum of intensities of all bands on the reducing gel.

The IgG variants were analyzed by SDS/PAGE followed by autoradiography (FIG. 5A). The protein yield from the codon optimized template was increased by 30% compared to the yield from the wild-type template. Under reducing conditions (e.g., in the DTT), the serine optimized anti-CD74 IgG was resolved into a heavy-chain band and a light-chain band. No prematurely terminated (e.g., aborted) protein product was generated from the codon optimized template compared to the wild-type template. In addition, the serine codon nucleic acid template produced significantly more protein than the wild-type template (FIG. 5B).

Reduced mass analysis was performed to investigate the presence of serine misincorporations into the anti-CD74 IgG subunits. Proteins are incubated in 4 M Gud HCl and 10 mM DTT for 30 minutes at 45° C., cool to room temperature, acidify and then store at 4-10° C. until the sample is run on the LC-MS. Mass spectra of proteins or antibody chains were deconvoluted using the Maximum Entropy algorithm from Agilent or the MaxEnt1 algorithm from Waters. Both programs produced a neutral mass spectrum from the observed charge envelope in the mass spectrum using an through an iterative algorithm.

No Ser-to-Asn substitutions were detected using the Ser-optimized light chain template in cell free synthesis reactions at 20° C. (FIGS. 6A and 6D), 25° C. (FIGS. 6B and 6E), or 30° C. (FIGS. 6C and 6F), regardless of the ratio of heavy chain to light chain. With the wildtype variants generated in cell free reactions performed at 20° C. (FIG. 6G), no misincorporation of Asn in place of Ser was detected, yet Asn was detected in the light chains produced from cell free reactions at 25° C. (FIG. 6H) and 30° C. (FIG. 6I).

Misincorporations of the anti-CD74 IgG serine codon optimized heavy chain were not observed in cell free synthesis reactions at 20° C. (FIGS. 7A and 7D), 25° C. (FIGS. 7B and 7E), or 30° C. (FIGS. 7C and 7F). However, Ser-to-Asn substitutions were seen in the wild-type heavy chain with the wild-type template in cell free reactions performed at 25° C. (FIG. 7H) and 30° C. (FIG. 7I), but not at 20° C. (FIG. 7G).

Example 4. Generating Serine Codon Optimized Genes (Nucleic Acid Templates) Encoding the Trastuzamab Heavy Chain (HC) and Light Chain (LC)

The wild-type amino acid sequences of the trastuzumab heavy chain and light chain are set forth, for example, in ChEMBL Accession No. CHEMBL1201585. Wild-type genes (DNA) coding for the trastuzumab heavy chain and light chain ("original sequence" or "v1") and serine codon optimized heavy chain and light chain ("optimized sequence" or "v2") gene were synthesized (DNA 2.0, Menlo Park, Calif.). The only difference between v1 and v2 is serine codon usage.

The wild-type trastuzumab heavy chain nucleic acid template contained 35 AGC codons (about 77% of the total serine codons were AGC), 4 TCG codons, 5 TCT codons, 6 TCC codons and no AGT or TCA codons. The wild-type trastuzumab light chain nucleic acid template had 23 AGC codons, 2 TCG codons, 3 TCT codons, 3 TCC codons and no AGT or TCA codons.

In contrast, the codon optimized trastuzumab heavy chain gene included no AGC or AGT codons, 13 TCG codons, 12 TCA codons, 12 TCT codons, and 13 TCC codons. The codon optimized light chain contained no AGC or AGT codons, 7 TCG codons, 8 TCA codons, 8 TCT codons and 8 TCC codons.

The nucleic acid templates separately encoding the trastuzumab heavy chain and light chain were used in a cell free protein synthesis reaction to produce full-length trastuzumab. The templates were co-expressed in the presence of DsbC or PDI to promote the formation of disulfide bonds, and in turn, proper protein folding and antibody assembly. The cell free protein synthesis reaction is described above in Example 2.

Figure 8:
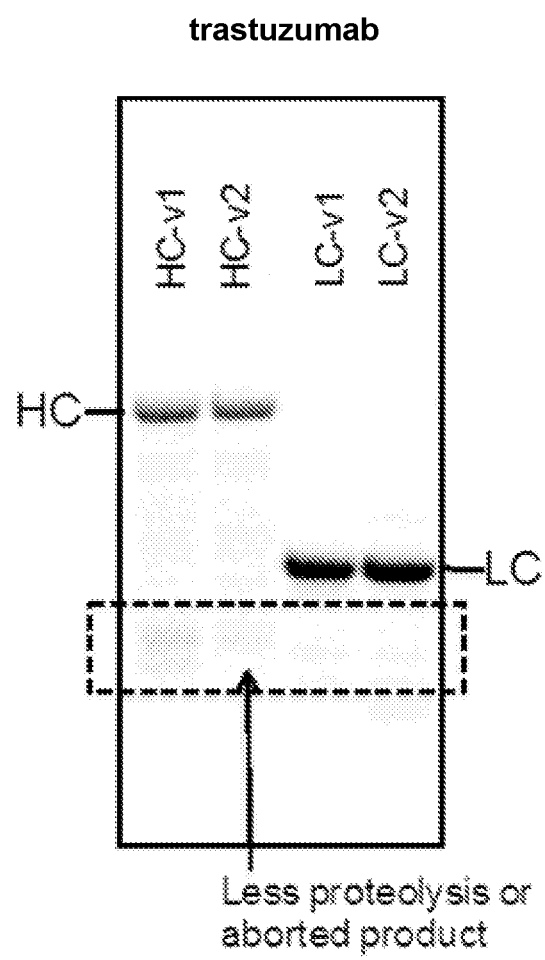
FIG. 8 shows that expression products encoded by serine codon optimized genes were subject to less proteolysis or aborted product.

The protein yield was quantified as described in Example 2. Briefly, $C^{14}$ labeled leucine was added to the cell free protein synthesis reaction and the reaction products were analyzed by SDS-PAGE followed by autoradiography. FIG. 8 shows that less proteolysis and aborted product was seen with the serine optimized trastuzumab heavy chain (HC-v2) and light chain (LC-v2) while proteolysis was observed for the non serine optimized heavy chain (HC-v1) and light chain (LC-v1).

The total IgG yield was also higher in CFPS reactions using the serine optimized templates for trastuzumab (FIG.

Figure 9:
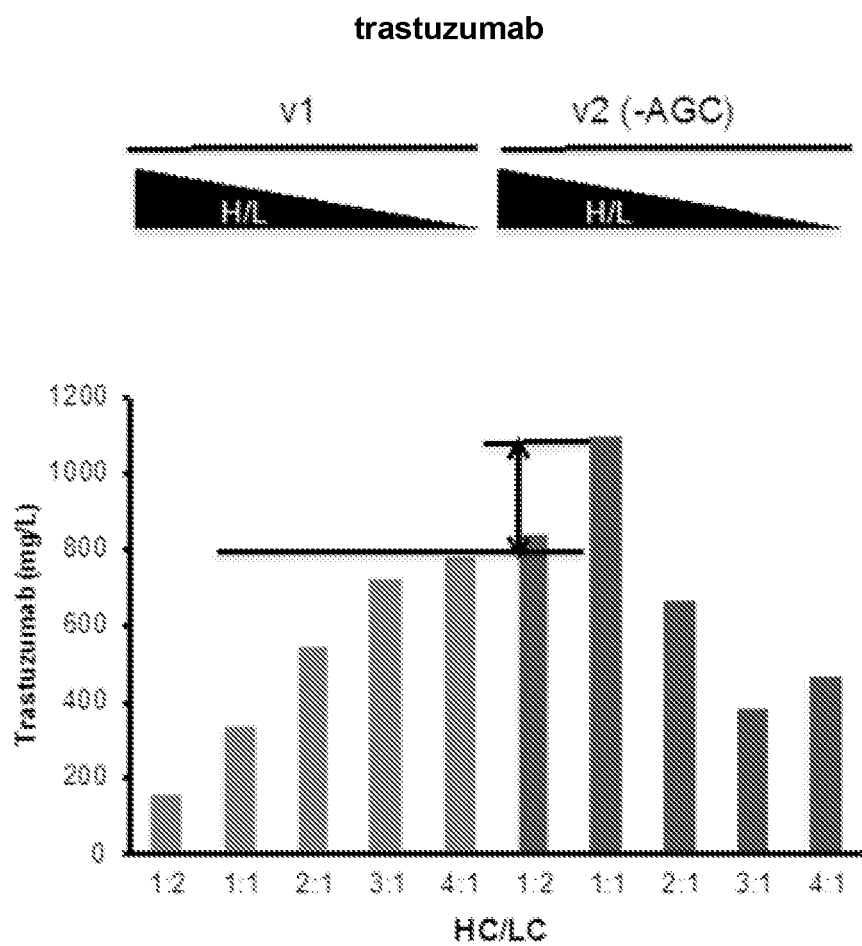
FIG. 9 show that trastuzumab yields were higher with serine codon optimized nucleic acid templates (genes), compared to the corresponding wild-type non-codon optimized genes.

9). The maximal yield was greater than 1000 mg/L when the ratio of serine optimized heavy chain template to serine optimized light chain template was 1:1. FIG. 9 shows that an optimal nucleic acid template ratio was easily determined using the serine optimized templates. By charting protein yield (e.g., IgG assembly) relative to increases in the heavy chain:light chain ratio, the optimal ratio was determined effectively and with confidence.

This example illustrates the advantages of using serine optimized nucleic acid templates encoding heavy chains and light chains in cell free protein synthesis reaction to produce antibodies. Such templates can result in greater (increased or higher) antibody yield, and less or no proteolytic products such as fewer or no prematurely terminated protein products, compared to non codon optimized templates. In addition, the de novo optimization of the heavy chain template to light chain template ratio can be performed more effectively and with a greater degree of confidence using serine optimized nucleic acid templates compared to non optimized templates.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for producing a full-length protein of interest in a cell free protein synthesis system said protein having multiple serine residues, the method comprising the steps of:
    i) combining a nucleic acid template encoding the full-length protein with a cell free protein synthesis system; wherein the template comprises codons encoding serine residues,
    wherein the template has been modified such that no more than 10% of the codons encoding serine residues are AGC,
    wherein at least one of the codons encoding serine residues in the template is AGT, TCA, or TCG; and
    ii) incubating the template and the cell free protein synthesis system under conditions permitting the translation of the protein of interest.

2. The method of claim 1, wherein the cell free protein synthesis system is derived from a bacterial cell.

3. The method of claim 2, wherein the bacterial cell is an *E. coli* cell.

4. The method of claim 1, wherein the cell free protein synthesis system has an active oxidative phosphorylation system.

5. The method of claim 1, wherein the protein of interest is an antibody or a fragment thereof.

6. The method of claim 5, wherein the antibody is IgG or IgE.

7. The method of claim 1, wherein the protein of interest is produced at a concentration of greater than 6 mg/liter.

8. The method of claim 1, wherein the protein of interest comprises amino acids wherein more than 15% of the amino acids are serine residues.

9. The method of claim 1, wherein the codons encoding serine residues are selected from the group comprising of AGT, TCA, TCC, TCG and TCT.

10. The method of claim 1, wherein the nucleic acid template has no AGC codons.

11. The method of claim 10, wherein the nucleic acid template has no AGT codons.

12. A combination of a nucleic acid template and a cell free protein synthesis system for producing a protein of interest having a plurality of serine residues, the combination comprising:
    a nucleic acid template encoding the protein of interest, wherein the nucleic acid template comprises codons encoding serine residues and wherein no more than 10% of the codons encoding the serine residues are AGC; and
    a cell free protein synthesis system.

13. The combination of claim 12, wherein the cell free protein synthesis system is derived from a bacterial cell.

14. The combination of claim 13, wherein the bacterial cell is an *E. coli* cell.

15. The combination of claim 12, wherein the cell free protein synthesis system has an active oxidative phosphorylation system.

16. The combination of claim 12, wherein the protein of interest is an antibody or a fragment thereof.

17. The combination of claim 16, wherein the antibody is IgG or IgE.

18. The combination of claim 12, wherein the protein of interest is produced at a concentration of greater than 6 mg/liter.

19. The combination of claim 12, wherein the protein of interest comprises amino acids wherein more than 15% of the amino acids are serine residues.

20. The combination of claim 12, wherein the codons encoding the serine residues are selected from the group comprising of AGT, TCA, TCC, TCG and TCT.

21. The combination of claim 12, wherein the nucleic acid template has no AGC codons.

22. The combination of claim 21, wherein the nucleic acid template has no AGT codons.

23. A nucleic acid encoding a full-length protein of interest having a plurality of serine residues,
    wherein the nucleic acid has been modified such that no more than 10% of the codons encoding the serine residues are AGC, and
    wherein at least one of the codons encoding serine residues in the nucleic acid is AGT, TCA, or TCG.

24. The nucleic acid of claim 23, wherein the protein of interest is an antibody.

25. The nucleic acid of claim 23, wherein the protein of interest comprises amino acids wherein more than 15% of the amino acids are serine residues.

26. The nucleic acid of claim 23, wherein the codons encoding serine residues are selected from the group consisting of AGT, TCA, TCC, TCG and TCT.

* * * * *